United States Patent [19]

Ward

[11] Patent Number: 4,568,378

[45] Date of Patent: Feb. 4, 1986

[54] HERBICIDAL 5-CYCLOALKYLAMINO-3-OXO-4-(SUBSTITUTED-PHENYL)-2,3-DIHYDROFURAN AND DERIVATIVES THEREOF

[75] Inventor: Carl E. Ward, San Jose, Calif.

[73] Assignee: Chevron Research Company, San Francisco, Calif.

[21] Appl. No.: 684,997

[22] Filed: Dec. 21, 1984

[51] Int. Cl.$^4$ .................. A01N 43/08; C07D 307/52
[52] U.S. Cl. ........................ 71/88; 549/477; 549/479
[58] Field of Search ............... 549/477, 479; 71/88

[56] References Cited

U.S. PATENT DOCUMENTS 4,441,910  4/1984  Shapiro ........................... 71/90

FOREIGN PATENT DOCUMENTS 42-19090  9/1967  Japan .
44-13710  6/1969  Japan .
1521092   8/1978  United Kingdom .
2080289   2/1982  United Kingdom .

OTHER PUBLICATIONS

Capraro et al., Helvetica Chimica Acta., vol. 66, No. 31, (1983), pp. 362–378.
Umio et al., Chemical Abstracts, vol. 70, (1969), 68123t.
Volovenko et al., Chemical Abstracts, vol. 95, (1981), 24799e.
Meier et al., Chemical Abstracts, vol. 94, (1981), 138818v.

Primary Examiner—Richard L. Raymond
Attorney, Agent, or Firm—T. G. DeJonghe; L. S. Squires

[57] ABSTRACT

5-cycloalkylamino-3-oxo-4-(substituted-phenyl)-2,3-dihydrofuran and derivatives thereof. The compounds generally exhibit both pre-emergence and post-emergence phytotoxicity and are useful as herbicides and also at low dosages as plant growth regulating agents.

38 Claims, No Drawings

HERBICIDAL 5-CYCLOALKYLAMINO-3-OXO-4-(SUBSTITUTED-PHENYL)-2,3-DIHYDROFURAN AND DERIVATIVES THEREOF

BACKGROUND OF THE INVENTION

This invention relates to 5-cycloalkylamino-3-oxo-4-(substituted-phenyl)-2,3-dihydrofuran derivatives and to the use of such compounds as herbicides and plant growth regulators.

Chemiker-Zeitung 104 (1980) No. 10, Pages, 302-303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application No. 13,710/69 (Chemical Abstracts 71:61195e) discloses the generic formula for 5-amino-3-oxo-4-(phenyl and halophenyl)-2,3-dihydrofuran and specifically discloses 5-amino-3-oxo-4-(phenyl and 4-chlorophenyl)-2,3-dihydrofurans. Japanese Pat. No. 19090 (Chemical Abstracts 69P10352e) discloses certain 2,3-dihydrothiophenes as pharmaceuticals. Helvetica Chemica Acta, Volume 66, Pages 362–378 (1983) discloses 5-N-cyclopropyl-4-phenyl-2-methoxycarbonyl-methylene-3-furanone as part of an academic chemical synthesis discussion. U.S. Pat. No. 4,441,910 discloses herbicidal ureidosulfonylfurans and ureidosulfonylthiophenes.

My U.S. application Ser. No. 607,610, filed May 9, 1984, and now abandoned discloses herbicidal compounds having the generic formula:

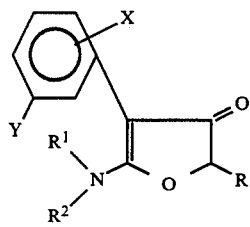

wherein R, R$^1$, X and Y can be certain substituents as will be subsequently defined and R$^2$ is hydrogen, alkyl, etc.

My prior U.S. application Ser. No. 623,805, filed June 22, 1984, discloses compounds having the formula:

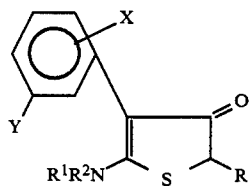

wherein R, R$^1$, R$^2$, X and Y are as defined above.

SUMMARY OF THE INVENTION

The present invention provides compounds having both pre-emergence and post-emergence herbicidal activity and having especially good pre-emergence activity against a broad spectrum of both broad-leaf weeds and grassy weeds. At lower application rates the compounds also exhibit plant growth regulating properties.

The compounds of the present invention can be represented by the following formula:

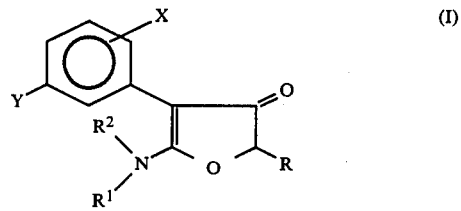

wherein R is lower alkyl having 1 through 4 carbon atoms; cycloalkyl having 3 through 7 carbon atoms, lower alkenyl having 2 through 6 carbon atoms; lower alkoxy having 1 through 4 carbon atoms; fluoro; fluoroalkyl having 1 through 4 carbon atoms and 1 through 3 fluoro atoms; alkenylmethoxy having 3 through 8 carbon atoms; haloalkenyl having 2 through 4 carbon atoms and 1 through 3 halo atoms independently selected from the group of fluoro, chloro, bromo, or iodo and wherein the halo atom is on a double bond carbon atom; lower alkoxyalkyl wherein the alkoxy and alkyl moiety thereof independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein said aryl moiety is phenyl, naphth-1-yl or inden-1-yl; or substituted aryl or arylalkylene selected from the group having the formulas:

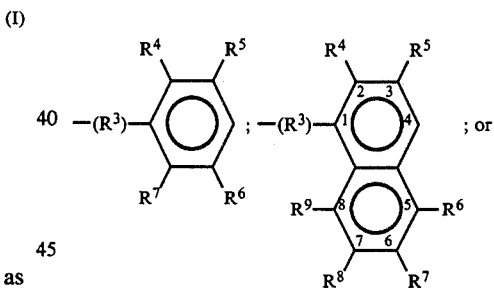

wherein one, two or three of R$^4$, R$^5$, R$^6$, R$^7$, R$^8$, and R$^9$ are independently selected from the group of lower alkyl, lower alkoxy, halo, nitro, or fluoroalkyl having 1 through 3 carbon atoms and 1 through 3 fluoro atoms, and the remainder are hydrogen; and R$^3$ is a single bond or an alkylene having 1 through 3 carbon atoms;

R$^1$ is hydrogen or alkyl having 1 through 4 carbon atoms;

R$^2$ is cyclopropyl or cyclobutyl;

X is hydrogen, lower alkyl, lower alkoxy, halo, or trifluoromethyl and can be at any available position on the phenyl ring; and Y is lower alkyl, lower alkoxy; halo; lower haloalkyl having 1 through 4 carbon atoms and 1 to 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms.

The invention also comprises compatible salts of the compound of Formula (I), for example salts obtained via replacement of the amino hydrogen (i.e., $R^1$ is hydrogen) with a compatible cation or enolation of the 3-oxo group following replacement of the amino hydrogen.

The compounds of Formula (I) exist as keto⇌enol isomers. The compounds also have an asymmetric carbon atoms and can also exist as optical isomers. In some instances the compounds also exist as geometric isomers. The above formula is intended to encompass the respective individual isomers as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 1 and 2 set forth hereinbelow on Pages 14–21 hereinbelow. In terms of substituents, the preferred compounds are those wherein R is lower alkyl, aryl or substituted aryl, more preferably methyl, ethyl, propyl, phenyl or substituted phenyl, and especially phenyl, monomethylphenyl or monohalophenyl, more especially methyl, ethyl, n-propyl, 2-halophenyl, 2-lower alkylphenyl, or 4-fluorophenyl. Preferably $R^1$ is hydrogen. Preferably $R^2$ is cyclopropyl.

The compounds of Formula I can be conveniently prepared by applying the general amination procedure described in the commonly assigned application of P. Pomidor, U.S. Ser. No. 666,078 filed Oct. 26, 1984. The preparation of the present compounds can be schematically represented by the following overall reaction equation.

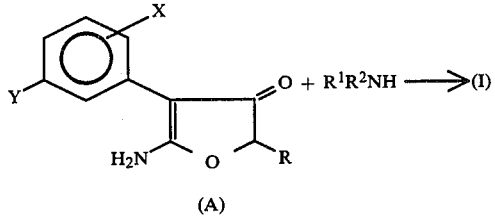

(A)

wherein R, $R^1$, $R^2$, X and Y are as defined herein above.

This process can be effected by contacting compound A with a primary or secondary amine (B), having the desired $R^1R^2$ groups, under reactive conditions, preferably in an inert organic solvent and water. Best results are obtained by using an aqueous amine.

Typically, this process is conducted at temperatures in the range of about from 65° to 125° C., preferably about from 65° to 80° C., for about from 1 to 200 hours, preferably about from 1 to 72 hours, using a large excess of amine (B); typically at least 20 moles of amine (B) per mole of compound A. More generally about from 20 to 500, and preferably, 150 to 300 moles of amine B are used per mole of compound A. Best results are generally obtained using an alcohol solvent. Preferably, the alcohol solvent is a liquid alkanol, for example, methanol, ethanol, and the like. Other inert organic solvents which can be used in place of the alcohol include, for example, tetrahydrofuran, dimethylformamide, dimethylsulfoxide, and the like, and compatible mixtures thereof. Typically, about from 0 to 30, preferably 10 to 20 parts by weight of alcohol or other solvent are used per part by weight of compound A. The process can also be carried out neat (i.e., without solvent).

As before noted, best results are obtained using aqueous amine. In some instances the amines are supplied commercially as aqueous solutions or the aqueous amine can be formed by adding water directly to the amine and adding the aqueous amine to the reaction mixture or by simply adding water to the reaction mixture. Where an aqueous amine is used, typically about from 0.1 to 10, preferably 0.5 to 4 parts by weight of water are used per part by weight of amine.

The products of Formula III can be recovered from their respective reaction product mixtures by any suitable separation and purification procedure, such as, for example, recrystallization and chromatography. Suitable separation and purification procedures are, for example, illustrated in the Examples set forth hereinbelow.

The compounds of Formula (A) can be prepared via the procedures described by my co-pending Application Ser. No. 607,610, filed May 9, 1984, now abandoned, which procedures are hereby incorporated by reference. The starting materials of Formula (A) where R is lower alkoxy or fluoro are preferably prepared via the procedures described in my co-pending Application Ser. No. 666,075, filed Oct. 26, 1984, which procedures are hereby incorporated by reference.

The compatible salts of Formula (I) can be prepared by conventional procedures for example by treating the compound of Formula (I) wherein $R^1$ is hydrogen with a suitable strong base such as, for example, n-butyllithium, sodium hydride, potassium hydride, and the like, having the desired cation, by conventional procedures to yield the corresponding $R^1$ cation salts. The enolate salts can be prepared by treating the $R^1$ cation salts with base via conventional procedures. Additional variations in the salt cation can also be effected via ion exchange with an ion exchange resin having the desired cation.

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mole ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example, $-CH_2-$; $-CH_2-CH_2-$;

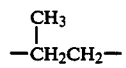

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group $-OR'$ wherein $R'$ is lower alkyl.

The term "lower alkylthio" refers to the group $-SR'$ wherein $R'$ is lower alkyl.

The term "lower alkoxyalkyl" refers to the group $R'OR''-$ wherein $R'$ and $R''$ are independently straight chain or branched chain alkyl groups having 1 through 3 carbon atoms.

The term "lower alkylthioalkyl" refers to the group $R'SR''-$ wherein $R'$ and $R''$ are independently straight chain or branched chain alkyl groups having 1 through 3 carbon atoms.

The term "lower alkoxycarbonylalkyl" refers to the group

wherein $R'$ is lower alkyl and $R''$ is alkylene having 1 through 4 carbon atoms and can be straight or branched chained. Typical alkoxycarbonylalkyl groups include for example, $-CH_2C(O)OCH_3$; $-CH(CH_3)-C(O)OC_2H_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro, 3-chloromethylphenyl, 2-nitro, 5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group $ArR^3-$ wherein Ar is aryl and $R^3$ is alkylene having 1 through 3 carbon atoms and includes both straight-chained and branched-chained alkylenes, for example, methylene, ethyl, 1-methylethyl, and propyl.

The term "(substituted aryl)alkylene" or "ring-substituted arylalkylene" refers to the group $Ar'R^3-$ wherein $Ar'$ is substituted aryl and $R^3$ is alkylene as defined with respect to arylalkylene.

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°-25° C.

UTILITY

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same type of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

2-Phenyl-3-oxo-4-(3-trifluoromethylphenyl)-5-cyclopropylamino-2,3-dihydrofuran

In this example, a mixture containing 5.0 g (0.0157 g mole) of 2-phenyl-3-oxo-4-(3-trifluoromethylphenyl)-5-amino-2,3-dihydrofuran and 8.96 g of cyclopropylamine in 50 ml of ethanol containing 5% water was refluxed for six days. At the end of this time, a sample of the reaction mixture was checked by thin layer chromatography and then an additional 8.96 g of cyclopropylamine was added. The mixture was refluxed for an additional 24 hours and then allowed to stand at room temperature over night. The mixture was then concentrated by evaporation under vacuum, affording a crude product oil. The crude product was chromatographed over silica gel eluting with 80:20 (V/V) petroleum ether and ethyl acetate. The product fractions were combined and evaporated in vacuo affording 2.07 g of the title compound Elemental Analysis Carbon calc.: 66.8%, found 67.4%; hydrogen calc.: 4.5%, found 4.7%; nitrogen calc.: 3.9%, found 4.6%; melting point 160°-164° C.

Similarly, by adopting the above procedure using the corresponding 2-substituted-3-oxo-4-(substituted phenyl)-5-amino-2,3-dihydrofuran compounds as starting material the following compounds can be respectively prepared.

2-phenyl-3-oxo-4-(5-chloro-3-trifluoromethylphenyl)-5-cyclopropylamino-2,3-dihydrofuran;
2-phenyl-3-oxo-4-(4-chloro-3-trifluoromethylphenyl)-5-cyclopropylamino-2,3-dihydrofuran;
2-phenyl-3-oxo-4-(2-bromo-3-trifluoromethylphenyl)-5-cyclopropylamino-2,3-dihydrofuran;
2-phenyl-3-oxo-4-(6-fluoro-3-trifluoromethylphenyl)-5-cyclopropylamino-2,3-dihydrofuran;
2-phenyl-3-oxo-4-(4-methyl-3-trifluoromethylphenyl)-5-cyclopropylamino-2,3-dihydrofuran;
2-phenyl-3-oxo-4-(5-methoxy-3-trifluoromethylphenyl)-5-cyclopropylamino-2,3-dihydrofuran;
2-phenyl-3-oxo-4-(6-methyl-3-trifluoromethylphenyl)-5-cyclopropylamino-2,3-dihydrofuran;
2-phenyl-3-oxo-4-(3,5-di-trifluoromethylphenyl)-5-cyclopropylamino-2,3-dihydrofuran;
2-phenyl-3-oxo-4-(3-difluoromethoxyphenyl)-5-cyclopropylamino-2,3-dihydrofuran;
2-phenyl-3-oxo-4-(3-trifluoromethoxyphenyl)-5-cyclopropylamino-2,3-dihydrofuran;
2-phenyl-3-oxo-4-(3-trifluoromethylthiophenyl)-5-cyclopropylamino-2,3-dihydrofuran;
2-(4-fluorophenyl)-3-oxo-4-(3-trifluoromethylphenyl)-5-cyclopropylamino-2,3-dihydrofuran;
2-(1-naphthyl)-3-oxo-4-(3-trifluoromethylphenyl)-5-cyclopropylamino-2,3-dihydrofuran;
2-phenyl-3-oxo-4-(2-chloro-3-methylphenyl)-5-cyclopropylamino-2,3-dihydrofuran;
2-phenyl-3-oxo-4-(4-ethyl-3-methylphenyl)-5-cyclopropylamino-2,3-dihydrofuran;
2-phenyl-3-oxo-4-(5-methoxy-3-chlorophenyl)-5-cyclopropylamino-2,3-dihydrofuran;
2-phenyl-3-oxo-4-(3-iodophenyl)-5-cyclopropylamino-2,3-dihydrofuran;
2-phenyl-3-oxo-4-(3-difluoromethylthiophenyl)-5-cyclopropylamino-2,3-dihydrofuran;
2-phenyl-3-oxo-4-(3-trifluoromethylthiophenyl)-5-cyclopropylamino-2,3-dihydrofuran;
2-phenyl-3-oxo-4-(3,5-diethoxyphenyl)-5-cyclopropylamino-2,3-dihydrofuran;
2-(2-nitrophenyl)-3-oxo-4-(3-bromophenyl)-5-cyclopropylamino-2,3-dihydrofuran;
2-phenyl-3-oxo-4-(2-chloro-3-methylphenyl)-5-cyclopropylamino-2,3-dihydrofuran;
2-(1-naphthyl)-3-oxo-4-(3-bromo-2-ethylphenyl)-5-cyclopropylamino-2,3-dihydrofuran;
2-(1-naphthyl)-3-oxo-4-(2,3-dimethylphenyl)-5-cyclopropylamino-2,3-dihydrofuran;
2-phenyl-3-oxo-4-(3-chlorophenyl)-5-cyclopropylamino-2,3-dihydrofuran;
2-phenyl-3-oxo-4-(3-methylphenyl)-5-cyclopropylamino-2,3-dihydrofuran;
2-phenyl-3-oxo-4-(3-butoxyphenyl)-5-cyclopropylamino-2,3-dihydrofuran;
2-phenyl-3-oxo-4-(2-propylphenyl)-5-cyclopropylamino-2,3-dihydrofuran;
2-phenyl-3-oxo-4-(3-bromophenyl)-5-cyclopropylamino-2,3-dihydrofuran;
2-(3-nitrophenyl)-3-oxo-4-(3-iodophenyl)-5-cyclopropylamino-2,3-dihydrofuran;
2-(2,3-dichlorobenzyl)-3-oxo-4-(2-trifluoromethylphenyl)-5-cyclopropylamino-2,3-dihydrofuran;
2-(1-naphthyl)-3-oxo-4-(3-methoxyphenyl)-5-cyclopropylamino-2,3-dihydrofuran;
2-(3-chloro-8-fluoronaphth-1-yl)-3-oxo-4-(3-trifluoromethylphenyl)-5-cyclopropylamino-2,3-dihydrofuran;
2-(2-trifluoromethyl-3-methyl-8-methoxynaphth-1-yl)-3-oxo-4-(3-trifluoromethylphenyl)-5-cyclopropylamino-2,3-dihydrofuran;
2-inden-1-yl-3-oxo-4-(3-trifluoromethylphenyl)-5-cyclopropylamino-2,3-dihydrofuran;
2-(2-fluoroinden-1-yl)-3-oxo-4-(3-trifluoromethylphenyl)-5-cyclopropylamino-2,3-dihydrofuran;
2-methyl-3-oxo-4-(3-trifluoromethylphenyl)-5-cyclopropylamino-2,3-dihydrofuran;
2-ethyl-3-oxo-4-(3-trifluoromethylphenyl)-5-cyclopropylamino-2,3-dihydrofuran;
2-ethyl-3-oxo-4-(5-chloro-3-trifluoromethylphenyl)-5-cyclopropylamino-2,3-dihydrofuran;
2-cyclopentyl-3-oxo-4-(3-trifluoromethylphenyl)-5-cyclopropylamino-2,3-dihydrofuran;
2-vinyl-3-oxo-4-(3-trifluoromethylphenyl)-5-cyclopropylamino-2,3-dihydrofuran;
2-allyl-3-oxo-4-(3-trifluoromethylphenyl)-5-cyclopropylamino-2,3-dihydrofuran;
2-allyl-3-oxo-4-(2-methoxy-3-trifluoromethylphenyl)-5-cyclopropylamino-2,3-dihydrofuran;
2-trifluoromethyl-3-oxo-4-(3-trifluoromethylphenyl)-5-cyclopropylamino-2,3-dihydrofuran;
2-methyl-3-oxo-4-(3-difluoromethoxyphenyl)-5-cyclopropylamino-2,3-dihydrofuran;
2-methyl-3-oxo-4-(3-trifluoromethoxyphenyl)-5-cyclopropylamino-2,3-dihydrofuran;
2-(2-chlorovinyl)-3-oxo-4-(3-trifluoromethylphenyl)-5-cyclopropylamino-2,3-dihydrofuran;
2-(2-chlorovinyl)-3-oxo-4-(5-nitro-3-trifluoromethylphenyl)-5-cyclopropylamino-2,3-dihydrofuran;
2-methyl-3-oxo-4-(2-methoxy-3-chlorophenyl)-5-cyclopropylamino-2,3-dihydrofuran;
2-ethyl-3-oxo-4-(2-chloro-3-fluorophenyl)-5-cyclopropylamino-2,3-dihydrofuran;
2-vinyl-3-oxo-4-(3-methyl-4-methoxyphenyl)-5-cyclopropylamino-2,3-dihydrofuran;
2-allyl-3-oxo-4-(3,6-dimethylphenyl)-5-cyclopropylamino-2,3-dihydrofuran;
2-trifluoromethyl-3-oxo-4-(3-trifluoromethyl-4-bromophenyl)-5-cyclopropylamino-2,3-dihydrofuran;
2-(2-chlorovinyl)-3-oxo-4-(3-nitro-4-methylphenyl)-3-oxo-5-cyclopropylamino-2,3-dihydrofuran;
2-methyl-3-oxo-4-(3-methoxyphenyl)-5-cyclopropylamino-2,3-dihydrofuran;
2-methyl-3-oxo-4-(3-difluoromethylthiophenyl)-5-cyclopropylamino-2,3-dihydrofuran;
2-methyl-3-oxo-4-(3-trifluoromethylthiophenyl)-5-cyclopropylamino-2,3-dihydrofuran;
2-ethyl-3-oxo-4-(3-chlorophenyl)-5-cyclopropylamino-2,3-dihydrofuran;
2-vinyl-3-oxo-4-(3-methylphenyl)-5-cyclopropylamino-2,3-dihydrofuran;
2-allyl-3-oxo-4-[3,5-di(trifluoromethyl)phenyl]-5-cyclopropylamino-2,3-dihydrofuran;
2-trifluoromethyl-3-oxo-4-(4-fluorophenyl)-5-cyclopropylamino-2,3-dihydrofuran;
2-(2-chlorovinyl)-3-oxo-4-(2-bromophenyl)-3-oxo-5-cyclopropylamino-2,3-dihydrofuran;
2-propyl-3-oxo-4-(2-methoxy-3-chlorophenyl)-5-cyclopropylamino-2,3-dihydrofuran;
2-butyl-3-oxo-4-(2-chloro-3-fluorophenyl)-5-cyclopropylamino-2,3-dihydrofuran;
2-vinyl-3-oxo-4-(3-chloro-4-methoxyphenyl)-5-cyclopropylamino-2,3-dihydrofuran;
2-allyl-3-oxo-4-(3,6-dimethylphenyl)-5-cyclopropylamino-2,3-dihydrofuran;

2-trifluoromethyl-3-oxo-4-(3-trifluoromethyl-5-bromophenyl)-5-cyclopropylamino-2,3-dihydrofuran;
2-(2-chlorovinyl)-3-oxo-4-(3-fluoro-4-methylphenyl)-3-oxo-5-cyclopropylamino-2,3-dihydrofuran;
2-phenyl-3-oxo-4-(3-methoxyphenyl)-5-cyclopropylamino-2,3-dihydrofuran;
2-methyl-3-oxo-4-(3,5-difluorophenyl)-5-cyclopropylamino-2,3-dihydrofuran;
2-vinyl-3-oxo-4-(3,5-diethylphenyl)-5-cyclopropylamino-2,3-dihydrofuran;
2-allyl-3-oxo-4-(3-propoxyphenyl)-5-cyclopropylamino-2,3-dihydrofuran;
2-trifluoromethyl-3-oxo-4-(3-fluorophenyl)-5-cyclopropylamino-2,3-dihydrofuran;
2-propyl-3-oxo-4-(2-bromophenyl)-3-oxo-5-cyclopropylamino-2,3-dihydrofuran;
2-phenyl-3-oxo-4-(2-iodo-3-fluorophenyl)-5-cyclopropylamino-2,3-dihydrofuran;
2-benzyl-3-oxo-4-(2-isopropoxy-3-trifluoromethylphenyl)-5-cyclopropylamino-2,3-dihydrofuran;
2-(3-chlorophenyl)-3-oxo-4-(2,3-dimethylphenyl)-5-cyclopropylamino-2,3-dihydrofuran;
2-naphth-1-yl-3-oxo-4-(3-trifluoromethyl-4-bromophenyl)-5-cyclopropylamino-2,3-dihydrofuran;
2-(3-methylphenyl)-3-oxo-4-(3-butyl-4-methylphenyl)-3-oxo-5-cyclopropylamino-2,3-dihydrofuran;
2-(3-fluorophenyl)-3-oxo-4-(3-chlorophenyl)-5-cyclopropylamino-2,3-dihydrofuran;
2-(2,3,5-trifluorophenyl)-3-oxo-4-(3-trifluoromethylphenyl)-5-cyclopropylamino-2,3-dihydrofuran; and
2-(3-methylnaphth-1-yl)-3-oxo-4-(3-trifluoromethylphenyl)-5-cyclopropylamino-2,3-dihydrofuran;
2-(1'-chlorovinyl)-3-oxo-4-(3-trifluoromethylphenyl)-5-cyclopropylamino-2,3-dihydrofuran;
2-fluoromethyl-3-oxo-4-(3-trifluoromethylphenyl)-5-cyclopropylamino-2,3-dihydrofuran;
2-methoxymethylene-3-oxo-4-(3-trifluoromethylphenyl)-5-cyclopropylamino-2,3-dihydrofuran;
2-propoxymethylene-3-oxo-4-(3-trifluoromethylphenyl)-5-cyclopropylamino-2,3-dihydrofuran;
2-ethoxymethylene-3-oxo-4-(3-trifluoromethylphenyl)-5-cyclopropylamino-2,3-dihydrofuran;
2-(2-methoxypropyl)-3-oxo-4-(3-trifluoromethylphenyl)-5-cyclopropylamino-2,3-dihydrofuran;
2-methylthiomethylene-3-oxo-4-(3-trifluoromethylphenyl)-5-cyclopropylamino-2,3-dihydrofuran; and
2-(1-propylthioethyl)-3-oxo-4-(3-trifluoromethylphenyl)-5-cyclopropylamino-2,3-dihydrofuran.
2-benzyl-3-oxo-4-(3-trifluoromethylphenyl)-5-cyclopropylamino-2,3-dihydrofuran;
2-(2-fluorobenzyl)-3-oxo-4-(3-trifluoromethylphenyl)-5-cyclopropylamino-2,3-dihydrofuran;
2-(3-methylbenzyl)-3-oxo-4-(3-trifluoromethylphenyl)-5-cyclopropylamino-2,3-dihydrofuran;
2-(2-ethoxybenzyl)-3-oxo-4-(3-trifluoromethylphenyl)-5-cyclopropylamino-2,3-dihydrofuran;
2-(3-nitrobenzyl)-3-oxo-4-(3-trifluoromethylphenyl)-5-cyclopropylamino-2,3-dihydrofuran;
2-(4-fluorobenzyl)-3-oxo-4-(3-trifluoromethylphenyl)-5-cyclopropylamino-2,3-dihydrofuran;
2-(2-trifluoromethylbenzyl)-3-oxo-4-(3-trifluoromethylphenyl)-5-cyclopropylamino-2,3-dihydrofuran;
2-(chloro-3-propylphenyl)-3-oxo-4-(3-trifluoromethylphenyl)-5-cyclopropylamino-2,3-dihydrofuran;
2-(2-nitro-3-methoxyphenyl)-3-oxo-4-(3-trifluoromethylphenyl)-5-cyclopropylamino-2,3-dihydrofuran;
2-(2,3-dichloro-6-methylbenzyl)-3-oxo-4-(3trifluoromethylphenyl)-5-cyclopropylamino-2,3-dihydrofuran;
2-(beta-phenethyl)-3-oxo-4-(3-trifluoromethylphenyl)-5-cyclopropylamino-2,3-dihydrofuran;
2-[3-(2-bromophenyl)propyl]-3-oxo-4-(3-trifluoromethylphenyl)-5-cyclopropylamino-2,3-dihydrofuran;
2-[1-methyl-2-(phenyl)ethyl]-3-oxo-4-(3-trifluoromethylphenyl)-5-cyclopropylamino-2,3-dihydrofuran;
2-naphth-1-ylmethylene-3-oxo-4-(3-trifluoromethylphenyl)-5-cyclopropylamino-2,3-dihydrofuran;
2-(2-fluoronaphth-1-ylmethylene)-3-oxo-4-(3-trifluoromethylphenyl)-5-cyclopropylamino-2,3-dihydrofuran;
2-(3-butylnaphth-1-ylmethylene)-3-oxo-4-(3-trifluoromethylphenyl)-5-cyclopropylamino-2,3-dihydrofuran;
2-(5-methoxynaphth-1-ylmethylene)-3-oxo-4-(3-trifluoromethylphenyl)-5-cyclopropylamino-2,3-dihydrofuran;
2-(6-nitronaphth-1-ylmethylene)-3-oxo-4-(3-trifluoromethylphenyl)-5-cyclopropylamino-2,3-dihydrofuran;
2-(7-trifluoromethylnaphth-1-ylmethylene)-3-oxo-4-(3-trifluoromethylphenyl)-5-cyclopropylamino-2,3-dihydrofuran;
2-(2-chloro-8-methylnaphth-1-ylmethylene)-3-oxo-4-(3-trifluoromethylphenyl)-5-cyclopropylamino-2,3-dihydrofuran;
2-(3-methoxy-5-nitro-7-fluoromethylnaphth-1-yl)-3-oxo-4-(3-trifluoromethylphenyl)-5-cyclopropylamino-2,3-dihydrofuran;
2-methoxy-3-oxo-4-(3-trifluoromethylphenyl)-5-cyclopropylamino-2,3-dihydrofuran;
2-(beta-naphth-1-ylethyl)-3-oxo-4-(3-trifluoromethylphenyl)-5-cyclopropylamino-2,3-dihydrofuran;
2-[beta-(8-fluoronaphth-1-yl)ethyl]-3-oxo-4-(3-trifluoromethylphenyl)-5-cyclopropylamino-2,3-dihydrofuran;
2-[1-(7-methoxynaphth-1-yl)ethyl]-3-oxo-4-(3-trifluoromethylphenyl)-5-cyclopropylamino-2,3-dihydrofuran;
2-inden-1-ylmethylene-3-oxo-4-(3-trifluoromethylphenyl)-5-cyclopropylamino-2,3-dihydrofuran; and
2-(2-fluoroinden-1-ylmethylene)-3-oxo-4-(3-trifluoromethylphenyl)-5-cyclopropylamino-2,3-dihydrofuran.

Similarly by applying the above procedure but replacing cyclopropylamine with a mole equivalent amount of cyclobutylamine the 2-cyclobutylamino analogs of the above compounds can be prepared; for example.

2-phenyl-3-oxo-4-(3-trifluoromethylphenyl)-5-cyclobutylamino-2,3-dihydrofuran;
2-(2-fluorophenyl)-3-oxo-4-(3-trifluoromethylphenyl)-5-cyclobutylamino-2,3-dihydrofuran;
2-(2-chlorophenyl)-3-oxo-4-(3-trifluoromethylphenyl)-5-cyclobutylamino-2,3-dihydrofuran;
2-(2-methylphenyl)-3-oxo-4-(3-trifluoromethylphenyl)-5-cyclobutylamino-2,3-dihydrofuran;
2-methyl-3-oxo-4-(3-trifluoromethylphenyl)-5-cyclobutylamino-2,3-dihydrofuran;
2-ethyl-3-oxo-4-(3-trifluoromethylphenyl)-5-cyclobutylamino-2,3-dihydrofuran;
2-propyl-3-oxo-4-(3-trifluoromethylphenyl)-5-cyclobutylamino-2,3-dihydrofuran;

Similarly by applying the above procedure but replacing cyclopropylamine with N-cyclopropyl-N-methylamine the corresponding 5-(N-cyclopropyl-N-methylamino) homologs of the above compounds can be prepared.

EXAMPLE 2

Lithium salt of 2-phenyl-3-oxo-4-(3-trifluoromethylphenyl)-5-cyclopropylamino-2,3-dihydrofuran In this example, 5.4 ml of 1.6M n-butyllithium in hexane is added dropwise to a stirred solution containing 2.86 g of 2-phenyl-3-oxo-4-(3-trifluoromethylphenyl)-5-cyclopropylamino-2,3-dihydrofuran in 25 ml of tetrahydrofuran at −30° C. The resulting mixture is stirred for 20 minutes and then concentrated in vacuo affording the title compound.

Similarly, by adapting the above procedure, the corresponding lithium salts of the compounds of Examples 1 can also be prepared.

EXAMPLE 3

In this example, the title compound of Example 1 (i.e., 2-phenyl-3-oxo-4-(3-trifluoromethylphenyl)-5-cyclopropylamino-2,3-dihydrofuran) was tested for herbicidal activity using the procedures described hereinbelow for pre-emergent and post-emergent activity against a variety of grasses and broad-leaf plants including one grain crop and one broad-leaf crop.

Pre-Emergent Herbicide Test

Pre-emergence herbicidal activity was determined in the following manner.

Test solutions of the test compound were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm² or in some instances as indicated in Table 1 hereinbelow, certain of the compounds were tested at a lower dosage of 15.6 micrograms/cm². The pot was watered and placed in a greenhouse. The pot was watered intermittenly and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1
Pre-Emergence Herbicidal Activity
Application Rate: 27.5 micrograms/cm², unless otherwise noted
% Phytotoxicity

| Broad-Leaf Plants | | | |
|---|---|---|---|
| Lambsquarter | Mustard | Pigweed | Soybean |
| 99 | 100 | 100 | 90 |

| Grasses | | | |
|---|---|---|---|
| Crabgrass | Watergrass | Wild Oats | Rice |
| 100 | 100 | 100 | 94 |

TABLE 2
Post-Emergence Herbicidal Activity
Application Rate: 27.5 micrograms/cm², unless otherwise noted
% Phytotoxicity

| Broad-Leaf Plants | | | |
|---|---|---|---|
| Lambsquarter | Mustard | Pigweed | Soybean |
| 30 | 80 | 50 | 30 |

| Grasses | | | |
|---|---|---|---|
| Crabgrass | Watergrass | Wild Oats | Rice |
| 40 | 30 | 25 | 0 |

As can be seen from the above tests the title compound of Example 1, (i.e., 2-phenyl-3-oxo-4-(3-trifluoromethylphenyl)-5-cyclopropylamino-dihydrofuran) exhibited excellent pre-emergence herbicidal activity and moderate to weak post-emergence herbicidal activity.

Obviously, many modifications and variations of the invention described hereinabove and below can be made without departing from the essence and scope thereof.

What is claimed is:

1. A compound having the formula:

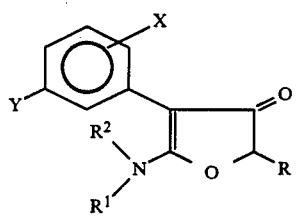

(I)

wherein R is lower alkyl, cycloalkyl having 3 through 7 carbon atoms; lower alkenyl having 2 through 6 carbon atoms; fluoro; fluoroalkyl having 1 through 4 carbon atoms and 1 through 3 fluoro atoms; lower alkoxy having 1 through 4 carbon atoms; alkenylmethoxy having 3 through 8 carbon atoms; haloalkenyl having 2 through 4 carbon atoms and 1 through 3 halo atoms independently selected from the group of fluoro, chloro, bromo, or iodo and wherein the halo atom is on a double bond carbon atom; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; aryalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

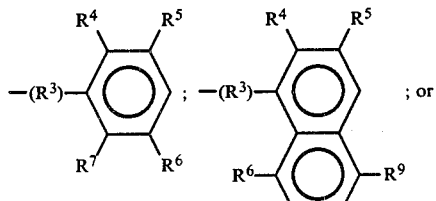

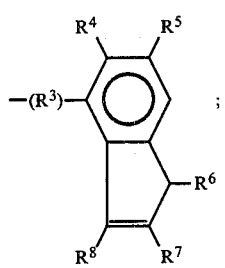

wherein
one, two or three of $R^4$, $R^5$, $R^6$, $R^7$, $R^8$, and $R^9$ are independently selected from the group of lower alkyl, lower alkoxy, halo, nitro, or fluoroalkyl having 1 through 3 carbon atoms and 1 through 3 fluoro atoms, and the remainder are hydrogen; and $R^3$ is a single bond or alkylene having 1 through 3 carbon atoms;
$R^1$ is hydrogen or alkyl having 1 through 4 carbon atoms;
$R^2$ is cyclopropyl or cyclobutyl;
X is hydrogen, lower alkyl, lower alkoxy, halo, or trifluoromethyl and can be at any available position on the phenyl ring; and Y is lower alkyl, lower alkoxy, halo, lower haloalkyl having 1 through 4 carbon atoms and 1 through 3 of the same or different halo atoms, lower haloalkoxy having 1 through 4 carbon atoms and 1 through 3 of the same or different halo atoms, or lower haloalkylthio having 1 through 4 carbon atoms and 1 through 3 of the same or different halo atoms;
and compatible salts thereof.

2. The compound of claim 1 wherein $R^1$ is hydrogen.
3. The compound of claim 2 wherein $R^2$ is cyclopropyl.
4. The compound of claim 1 wherein $R^2$ is cyclobutyl.
5. The compound of claim 1 wherein X is hydrogen.
6. The compound of claim 2 wherein X is hydrogen.
7. The compound of claim 3 wherein X is hydrogen.
8. The compound of claim 1 wherein R is phenyl, naphth-1-yl, 4-fluorophenyl or substituted aryl.
9. The compound of claim 8 wherein R is phenyl, naphthyl or a monosubstituted phenyl.
10. The compound of claim 9 wherein R is phenyl, halophenyl, or lower alkylphenyl.
11. The compound of claim 10 wherein R is phenyl, 4-fluorophenyl, 2-fluorophenyl, 2-chlorophenyl or 2-lower alkylphenyl.
12. The compound of claim 11 wherein X is hydrogen and $R^1$ is hydrogen or methyl.
13. The compound of claim 1 wherein R is lower alkyl, cycloalkyl, lower alkenyl, fluoroalkyl or haloalkenyl.

14. The compound of claim 13 wherein $R^1$ is hydrogen.
15. The compound of claim 14 wherein R is methyl, ethyl or propyl.
16. The compound of claim 15 wherein $R^2$ is cyclobutyl.
17. The compound of claim 16 wherein X is hydrogen.
18. A compound having the formula:

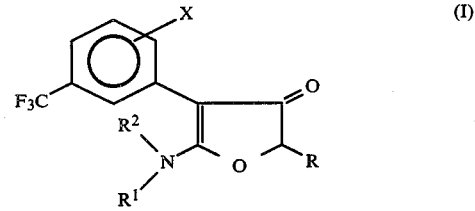

wherein R is lower alkyl, cycloalkyl having 3 through 7 carbon atoms; lower alkenyl having 2 through 6 carbon atoms; fluoro; fluoroalkyl having 1 through 4 carbon atoms and 1 through 3 fluoro atoms; lower alkoxy having 1 through 4 carbon atoms; alkenylmethoxy having 3 through 8 carbon atoms; haloalkenyl having 2 through 4 carbon atoms and 1 through 3 halo atoms independently selected from the group of fluoro, chloro, bromo, or iodo and wherein each halo substituent is on a double bond carbon atom; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

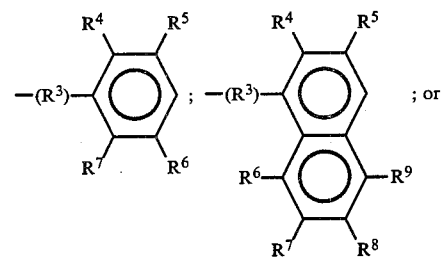

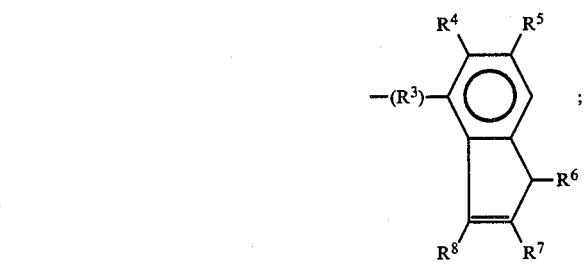

wherein
one, two or three of $R^4$, $R^5$, $R^6$, $R^7$, $R^8$, and $R^9$ are independently selected from the group of lower alkyl, lower alkoxy, halo, nitro, or fluoroalkyl having 1 through 3 carbon atoms and 1 through 3 fluoro atoms; and the remainder are hydrogen; and $R^3$ is a single bond or alkylene having 1 through 3 carbon atoms;

$R^1$ is hydrogen or alkyl having 1 through 4 carbon atoms;

$R^2$ is cyclopropyl or cyclobutyl;

X is hydrogen, lower alkyl, lower alkoxy, halo, or trifluoromethyl and can be at any available position on the phenyl ring;

and compatible salts thereof.

19. The compound of claim 18 wherein $R^1$ is hydrogen or methyl and $R^2$ is cyclopropyl.

20. The compound of claim 18 wherein $R^1$ is hydrogen or methyl and $R^2$ is cyclobutyl.

21. The compound of claim 18 wherein $R^1$ is hydrogen.

22. The compound of claim 21 wherein X is hydrogen and R is phenyl, naphthyl, 4-fluorophenyl, 2-halophenyl or 2-lower alkylphenyl.

23. The compound of claim 22 wherein $R^2$ is cyclopropyl.

24. The compound of claim 23 wherein R is phenyl, 2-fluorophenyl, 2-chlorophenyl or 2-methylphenyl.

25. The compound of claim 23 wherein R is phenyl.

26. The compound of claim 23 wherein R is 2-fluorophenyl.

27. The compound of claim 23 wherein R is 2-chlorophenyl.

28. The compound of claim 18 wherein R is lower alkyl, cycloalkyl, lower alkenyl, lower haloalkyl or lower haloalkenyl.

29. The compound of claim 28 wherein $R^1$ is hydrogen or methyl.

30. The compound of claim 29 wherein R is methyl, ethyl or propyl.

31. The compound of claim 30 wherein $R^1$ is hydrogen and $R^2$ is cyclopropyl.

32. The compound of claim 29 wherein X is hydrogen.

33. The compound of claim 18 wherein X is hydrogen.

34. A herbicidal composition comprising a herbicidally effective amount of a compound according to claim 1, or mixtures of such compounds, and a compatible carrier.

35. A herbicidal composition comprising a herbicidally effective amount of a compound according to claim 18, or mixtures thereof, and a compatible carrier.

36. A method for preventing or destroying plants which comprises applying a herbicidally effective amount of a compound according to claim 1, or mixtures thereof, to the foliage or potential growth medium of said plants.

37. A method for preventing or destroying plants which comprises applying a herbicidally effective amount of a compound according to claim 18, or mixtures thereof, to the foliage or potential growth medium of said plants.

38. A method for regulating the growth of plants which comprises applying to the foliage of said plants or their growth medium an amount of a compound according to claim 1, or mixtures thereof, effective to alter the growth pattern of such plants.

* * * * *